United States Patent
Carlucci et al.

(10) Patent No.: US 7,537,832 B2
(45) Date of Patent: May 26, 2009

(54) SUPERABSORBENT MATERIAL AND ABSORBENT ARTICLES CONTAINING SAID MATERIAL

(75) Inventors: Giovanni Carlucci, Chieti (IT); Antonella Pesce, Pescara (IT); Adelia Alessandra Tordone, Pescara (IT); Maurizio Tamburro, Sambuceto San Giovanni Teatino (IT)

(73) Assignee: The Procter & Gamble Company, Cincinnati, OH (US)

( * ) Notice: Subject to any disclaimer, the term of this patent is extended or adjusted under 35 U.S.C. 154(b) by 433 days.

(21) Appl. No.: 11/021,634

(22) Filed: Dec. 22, 2004

(65) Prior Publication Data

US 2005/0154364 A1 Jul. 14, 2005

(30) Foreign Application Priority Data

Dec. 23, 2003 (EP) .................................. 03104966

(51) Int. Cl.
*B32B 5/16* (2006.01)
(52) U.S. Cl. .................... 428/402; 428/403; 428/304.4; 428/311.11; 428/317.8; 428/537.5; 442/153; 442/167; 442/168; 442/171; 604/366; 604/367
(58) Field of Classification Search ............... 428/317.8, 428/537.5, 304.4, 311.11, 402, 403; 442/153, 442/167, 168, 171; 604/366, 367
See application file for complete search history.

(56) References Cited

U.S. PATENT DOCUMENTS

| | | | |
|---|---|---|---|
| 6,270,794 B1 | 8/2001 | Cilento et al. | |
| 6,833,488 B2 * | 12/2004 | Bucevschi et al. | .......... 604/368 |
| 6,844,430 B2 * | 1/2005 | Pesce et al. | .................... 536/20 |
| 6,887,564 B2 * | 5/2005 | Gagliardini et al. | ...... 428/317.9 |
| 2002/0007166 A1 | 1/2002 | Mitchell et al. | |
| 2002/0150761 A1 | 10/2002 | Lange et al. | |
| 2003/0068944 A1 | 4/2003 | Carlucci et al. | |
| 2003/0138631 A1 | 7/2003 | Mitchell et al. | |
| 2004/0166307 A1 | 8/2004 | Tamburro et al. | |
| 2004/0167487 A1 | 8/2004 | Tamburro et al. | |
| 2005/0013992 A1 | 1/2005 | Azad et al. | |
| 2005/0090586 A1 * | 4/2005 | Kang et al. | ................... 524/27 |

FOREIGN PATENT DOCUMENTS

WO   WO 02/30480 A1   4/2002

OTHER PUBLICATIONS

Knill C.J. et al., "Alginate Fibres Modified With Unhydrolysed and Hydrolysed Chitosans For Wound Dressings" Jan. 1, 2004, Carbohydrate Polymers, Applied Science Publishers, Ltd., Barking, GB, pp. 65-76.

* cited by examiner

*Primary Examiner*—Leszek Kiliman
(74) *Attorney, Agent, or Firm*—Amanda T. Barry; Kevin C. Johnson

(57) ABSTRACT

The present invention relates to the field of absorbent articles for personal hygiene. Specifically, the present invention provides a superabsorbent material having improved absorbency of complex fluids, such as body fluids like menses. Preferred absorbent articles for personal hygiene in the context of the present invention are feminine care absorbent articles.

20 Claims, No Drawings

SUPERABSORBENT MATERIAL AND ABSORBENT ARTICLES CONTAINING SAID MATERIAL

CROSS REFERENCE TO RELATED APPLICATIONS

1. Field of Invention

The present invention relates to the field of absorbent articles for personal hygiene. Specifically, the present invention provides a superabsorbent material having improved absorbency of complex fluids, such as body fluids like menses. Preferred absorbent articles for personal hygiene in the context of the present invention are feminine care absorbent articles.

2. Background of the Invention

Superabsorbents for absorbing aqueous fluids are known in the art since long. Especially in the field of infant diapers materials like more or less cross-linked polyacrylates are widely used. However, although these materials are very well suited for absorbing simple aqueous fluids like urine, they have proven to be of less utility when used for absorbing more complex aqueous fluids, like blood and menses. Menses contain high amounts of materials, which tend to block the polyacrylates. Such materials are metal ions, which interact with the carboxylic groups of the polyacrylates. Other such materials in menses are proteins, fatty acids and cell debris.

It is known from EP-A-1,276,511 to combine absorbent gelling materials with chitosan material in agglomerated particles of both materials for odour control in absorbent articles. However, due to the random nature of such an agglomeration procedure the distribution of chitosan and absorbent gelling material in such agglomerated particles is quite unpredictable. This results in particles having an excess of chitosan for instance or particles with chitosan only in their interior, which would clearly detriment the intended functionality.

There is thus a need for providing a superabsorbent material being capable of efficiently absorbing complex aqueous fluids like menses.

SUMMARY OF THE INVENTION

The present invention provides a superabsorbent material comprising multicomponent particles by combining an acidic superabsorbent resin with gel-forming polysaccharides, which gelify and thus immobilize in their circumference materials contained in menses (e.g. proteins, fatty acids and the like), which would otherwise block the superabsorbent resin. The gel-forming polysaccharides form microdomains, which are present at least on the surface of the superabsorbent resin particles. This ensures that the gel-forming polysaccharides have a maximized effective surface for interacting with the menses.

In a particularly preferred embodiment of the multicomponent particles herein said microdomains are present on the surface of the superabsorbent resin particles only. By this it is ensured that only the parts of the superabsorbent resin particles having primary exposure to menses are provided with gel-forming polysaccharides. This construction optimizes polysaccharide usage when producing the superabsorbent material disclosed herein.

In another preferred embodiment herein the gel-forming polysaccharides are acidic, having a pH of from 3to 6.

In another, particularly preferred embodiment herein the gel-forming polysaccharides are constituted of acidic chitosan salts, preferably selected from chitosonium pyrrolidone carboxylate and chitosonium lactate or mixtures thereof.

All documents cited are, in relevant part, incorporated herein by reference; the citation of any document is not to be construed as an admission that it is prior art with respect to the present invention.

DETAILED DESCRIPTION OF THE INVENTION

'Superabsorbent resin' as used herein refers to materials, which are capable of absorbing at least ten times their on weight of water. Examples for the superabsorbent resin herein are partially neutralized, acidic polyacrylic materials. The superabsorbent resin herein is a particulate material.

'Particulate material' or 'particles' herein refers to materials, which are present as a multiplicity of discrete particles, i.e. in the form of fibres, flakes, granules, beads or the like. In a preferred embodiment herein the superabsorbent resin is present in the form of granules having an average diameter in the range from 30 µm to 2 mm, preferably from 100 µm to 1 mm.

'Average diameter' as used herein refers to the largest cross-sectional length of a piece of material.

'Acidic' as used herein refers to the property of a material to establish a pH lower than 7 in an aqueous solution.

The superabsorbent material of the present invention comprises multicomponent particles being constituted of acidic superabsorbent resin particles, which are provided with microdomains of at least one gel-forming polysaccharide at least on their surface.

The superabsorbent resin herein has preferably a high grade of neutralization that results in high concentration of negatively charged groups. The pH of the preferred slightly neutralized superabsorbent resin ranges from 3.5 to 6. The superabsorbent resin can be any material having superabsorbent properties in which the functional groups are anionic, namely sulphonic groups, sulphate groups, phosphate groups or carboxyl groups. Preferably the functional groups are carboxylic groups. Particularly preferred anionic superabsorbent resins for use herein are synthetic anionic superabsorbent resins.

Generally the functional groups are attached to a slightly cross-linked acrylic base polymer. For example the base polymer may be a polyacrylamide, polyvinyl alcohol, ethylene maleic anhydride copolymer, polyvinylether, polyvinyl sulphonic acid, polyacrylic acid, polyvinylpyrrolidone and polyvinylmorpholine. Copolymers of these monomers can also be used.

Particular base polymers include cross-linked polyacrylates, hydrolyzed acrylonitrile grafted starch, starch polyacrylates and isobutylene maleic anhydride copolymers.

Such materials form hydrogels on contact with water (e.g., with urine, blood, and the like). One highly preferred type of hydrogel-forming, superabsorbent resin is based on polyacids, especially polyacrylic acid. Hydrogel-forming polymeric materials of this type are those which, upon contact with fluids (i.e., liquids) such as water or body fluids, imbibe such fluids and thereby form hydrogels. These preferred superabsorbent resins will generally comprise substantially water-insoluble, slightly cross-linked, partially neutralized, hydrogel-forming polymer materials prepared from polymerisable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, the preferred superabsorbent resins include hydrolyzed acrylonitrile grafted starch, acrylic acid grafted starch, polyacrylates, maleic anhydride-based copolymers and combinations thereof. Especially preferred anionic superabsorbent resins are the polyacrylates and acrylic acid grafted starch.

Whatever the nature of the polymer components of the preferred superabsorbent resins, such materials can be slightly cross-linked. Crosslinking serves to render these preferred hydrogel-forming absorbent materials substantially water-insoluble, and cross-linking also in part determines the gel volume and extractable polymer characteristics of the hydrogels formed therefrom. Suitable cross-linking agents are well known in the art and include, for example, (1) compounds having at least two polymerisable double bonds; (2) compounds having at least one polymerisable double bond and at least one functional group reactive with the acid-containing monomer material; (3) compounds having at least two functional groups reactive with the acid-containing monomer materials; and (4) polyvalent metal compounds which can from ionic cross-linkages. Cross-linking agents of the foregoing types are described in greater detail in Masuda et al; U.S. Pat. No. 4,076,663; issued Feb. 28, 1978. Preferred cross-linking agents are the di- or polyesters of unsaturated mono- or polycarboxylic acids with polyols, the bisacrylamides and the di- or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the gelling materials used herein.

The preferred superabsorbent resin used herein are those which have a relatively high capacity for imbibing fluids encountered in the absorbent articles; this capacity can be quantified by referencing the "gel volume" of said superabsorbent resin. Gel volume can be defined in terms of the amount of synthetic urine absorbed by any given absorbent gelling agent buffer and is specified as grams of synthetic urine per gram of gelling agent.

Gel volume in synthetic urine (see Brandt, et al, below) can be determined by forming a suspension of about 0.1-0.2 parts of dried superabsorbent resin to be tested with about 20 parts of synthetic urine. This suspension is maintained at ambient temperature under gentle stirring for about 1 hour so that swelling equilibrium is attained. The gel volume (grams of synthetic urine per gram of superabsorbent resin) is then calculated from the weight fraction of the gelling agent in the suspension and the ratio of the liquid volume excluded from the formed hydrogel to the total volume of the suspension. The preferred superabsorbent resin useful in this invention will have a gel volume of from about 20 to 70 grams, more preferably from about 25 to 60 grams, of synthetic urine per gram of superabsorbent resin.

Another feature of the most highly preferred superabsorbent resin relates to the level of extractable polymer material present in said materials. Extractable polymer levels can be determined by contacting a sample of preferred superabsorbent resin with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issues Mar. 31, 1987, reissue 32,649. The superabsorbent resin which are especially useful in the absorbent articles herein are those which have an equilibrium extractable content in synthetic urine of no more than about 17%, preferably no more than about 10% by weight of the superabsorbent resin.

The preferred, slightly cross-linked, hydrogel-forming superabsorbent resin will generally be employed in their partially neutralized form. For purposes described herein, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to as the "degree of neutralization". Typically, commercial anionic superabsorbent resins have a degree of neutralization somewhat from 25% to 90%.

The superabsorbent resins herein before described are typically used in the form of discrete particles. Such superabsorbent resin can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of superabsorbent resin particles may also be used.

The size of the superabsorbent resin particles may vary over a wide range. For reason of industrial hygiene, average particle sizes smaller than about 30 μm are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Preferred for use herein are superabsorbent resin particles substantially all of which have a particle size of from about 30 μm to about 2 mm. "Particle Size" as used herein means the weighted average of the smallest dimension of the individual particles.

For forming the multicomponent particles the superabsorbent resin particles are provided with at least one gel-forming polysaccharide on at least their surface. The gel-forming polysaccharides are provided to the superabsorbent resin particles as microdomains, which are present at least on the surface of the superabsorbent resin particles. 'Microdomains' as used herein refers to a discrete region within or on the surface of a multicomponent particle, which region is constituted by gel-forming polysaccharide. The microdomains have an average diameter in the range from 1 nm to 200 μm, preferably from 20 nm to 100 μm, more preferable from 30 nm to 1 μm and most preferably from 40 nm to 800 nm. The microdomains can touch each other so that in one embodiment the whole surface of the superabsorbent resin particles is covered with the gel-forming polysaccharides. In another preferred embodiment the microdomains do not cover more than 70% of the total surface of the superabsorbent resin particles. The advantage of this embodiment is that only the surface area of the superabsorbent resin particle, which has primary contact to complex body fluids like menses, is provided with gel-forming polysaccharide, which results in very efficient polysaccharide usage. In a further preferred embodiment the microdomains constitute not more than 90% of the overall volume of a superabsorbent resin particle. The advantage of the small size-of the microdomains is that the active surface of the gel-forming polysaccharide, i.e. the surface exposed to the menses, is very high with respect to the weight of gel-forming polysaccharide used.

'Gel-forming polysaccharide' as used herein means a polysaccharide material, which is capable to gelify aqueous fluids. Gel-forming polysaccharide herein specifically also means polysaccharides being able to bind electrolyte-containing fluids like body fluids. Gel-forming polysaccharides according to the definition herein act electrostatically on nearby negatively charged molecules and thereby hold them in their circumference. Positively charged cationic groups (e.g., quaternary ammonium groups in chitosan) of the gel-forming polysaccharides will interact with negatively charged anionic function-bearing molecules present in bodily fluids, like for example the carboxylic groups of proteins or fatty acids. This will result in the formation of a three-dimensional network between the chitosan material and such molecules with anionic groups (gelification of the bodily fluids). This gelification will further entrap other molecules present in body fluids (like lipids, acids).

Examples for the gel-forming polysaccharide herein are gum arabicum, locust bean gum, agar agar, alginate, gellan gum, carageenan, pectin, xanthan gum, glucomannan, laminarin, dextran, chitin or guar gum. Preferred gel-forming polysaccharides are chitosan materials, with acidic chitosan materials being especially preferred, which have a pH in the range from 3 to 6. Particularly preferred gel-forming polysaccharides are acidic chitosan salts, especially chitosonium pyrrolidone carboxylate and chitosonium lactate. The latter materials have proven to be exceptionally efficient with respect to gelify materials in menses, which would otherwise block the superabsorbent resin. In certain embodiments it might be beneficial to cross-link the gel-forming polysaccharides in order to reduce their water-solubility and to increase their gel strength.

The multicomponent particles of the superabsorbent material of the present invention are superior over the prior art in terms of absorption of complex fluids like menses because of the combination of two specific mechanisms: On one hand the high capacity for water absorption of the acidic superabsorbent resin and on the other the ability of the gel-forming polysaccharides to bind components of complex fluids, which would otherwise block the superabsorbent resin, by gelification. By this it is facilitated that the superabsorbent resins remains substantially unblocked and can fulfil its function of absorbing aqueous fluids to an optimum extend. As outlined before, in a preferred embodiment the microdomains according to the present invention are present on the surface of the multicomponent particles only. This provides the advantage of optimized gel-forming polysaccharide usage because this material is then only present in the area of contact of the multicomponent particles with e.g. the menses. On the other hand, as said before as well, it is beneficial not to cover the whole surface of the multicomponent particles by gel-forming polysaccharides, because otherwise the aqueous fluids could hardly approach the superabsorbent resin for being absorbed. Furthermore, the smaller the microdomains are the higher is their active surface. Thus, when using very small microdomains, especially microdomains having average diameters in the nanometre range, the same beneficial effect can be achieved with a small amount of gel-forming polysaccharide compared to a higher amount of larger microdomains.

By 'chitosan material', it is meant herein chitosans, modified chitosans, crosslinked chitosans, chitosan salts or mixtures thereof. Chitosan is a partially or fully deacetylated form of chitin, a naturally occurring polysaccharide. Indeed, chitosan is an aminopolysaccharide usually prepared by deacetylation of chitin (poly-beta-(1,4)-N-acetyl-D-glucosamine).

Chitosan is not a single, definite chemical entity but varies in composition depending on the conditions of manufacture. It may be equally defined as chitin sufficiently deacetylated to form soluble amine salts. Chitosan is the beta-(1,4)-polysaccharide of D-glucosamine and is structurally similar to cellulose, except that the C-2 hydroxyl group in cellulose is substituted with a primary amine group in chitosan. The large number of free amine groups makes chitosan a polymeric weak base. Solutions of chitosan are generally highly viscous, resembling those of natural gums.

The chitosan used herein is suitably in relatively pure form. Methods for the manufacture of pure chitosan are well known. Generally, chitin is milled into a powder and demineralised with an organic acid such as acetic acid. Proteins and lipids are then removed by treatment with a base, such as sodium hydroxide, followed by chitin deacetylation by treatment with concentrated base, such as 40 percent sodium hydroxide. The chitosan formed is washed with water until the desired pH is reached.

The properties of chitosan relate to its polyelectrolyte and polymeric carbohydrate character. Thus, it is generally insoluble in water, in alkaline solutions at pH levels above about 7, or in hydrophobic organic solvents. It generally dissolves readily in dilute aqueous solutions of organic acids such as formic, acetic, tartaric, glycolic, lactic and citric acids and also in dilute aqueous solutions of mineral acids, except, for example, sulphuric acid. In general, the amount of acid required to dissolve chitosan is approximately stoichiometric with the amino groups. Since the $pK_a$ for the amino groups present in chitosan is between 6.0 and 7.0, they can be protonated in very dilute acids or even close to neutral conditions, rendering a cationic nature to this biopolymer. This cationic nature is the basis of many of the benefits of chitosan. Indeed, chitosan material can be considered as a linear polyelectrolyte with a high charge density which can interact with negatively charged surfaces, like proteins (e.g. by interfering with the proteinic wall construction of microorganisms, thereby acting as an antimicrobial agent and/or by reacting with the proteins present in bodily fluid, like menses, thereby acting as a gelifying agent for such fluid).

Without wishing to be bound by any theory, it is believed that chitosan material retains electrolyte-containing fluids like body fluids by multiple mechanisms.

One mechanism is conventional absorption by incorporation of the water dipole molecules into the structure. As the quaternary ammonium groups, being positively charged, are distracting each other, molecular cavities exist, in which water molecules can penetrate. By the penetration of dipole molecules, like water, these cavities can be widened by swelling and thereby generating even more space for further water molecules. This mechanism can be continued until the limits of molecular tension are reached.

The second mechanism of binding electrolyte-containing fluids, like body fluids, by chitosan material is gelification. Chitosan material acts electrostatically on nearby negatively charged molecules and thereby holds them in its circumference. The positively charged cationic groups (e.g., quaternary ammonium groups) of the chitosan material will interact with negatively charged anionic function-bearing molecules present in bodily fluids, like for example the carboxylic groups of proteins. This will result in the formation of a three-dimensional network between the chitosan material and such molecules with anionic groups (gelification of the bodily fluids). This gelification will further entrap other molecules present in body fluids (like lipids, acids). Due to the gelification properties of the chitosan material with respect to electrolyte-containing fluids, a liquid barrier is generated when the chitosan material is wetted by such fluids.

Preferred chitosan materials for use herein have an average degree of deacetylation (D.A.) of more than 70%, preferably from 80% to about 100%. The degree of deacetylation refers to the percentage of the amine groups that are deacetylated. This characteristic is directly related to the hydrogen bonding existing in this biopolymer, affecting its structure, solubility and ultimately its reactivity. The degree of deacetylation can be determined by titration, dye adsorption, UV/vis, IR and NMR spectroscopy. The degree of deacetylation will influence the cationic properties of chitosan. By increasing the degree of deacetylation the cationic character of the chitosan material will increase and thus also its gelifying abilities.

Suitable chitosan materials to use herein include substantially water-soluble chitosan. As used herein, a material will be considered water-soluble when it substantially dissolves in excess water to form a clear and stable solution, thereby, losing its initially particulate form and becoming essentially molecularly dispersed throughout the water solution. Preferred chitosan materials for use herein are water soluble, i.e. at least 1 gram and preferably at least 3 gram of the chitosan materials are soluble in 100 grams of water at 25° C. and one atmosphere. By 'solubility' of a given compound it is to be understood herein the amount of said compound solubilised in deionised water at 25° C. and one atmosphere in absence of a precipitate. Generally, the water-soluble chitosan materials will be free from a higher degree of crosslinking, as crosslinking tends to render the chitosan materials water insoluble.

Chitosan materials may generally have a wide range of molecular weights. Chitosan materials with a wide range of molecular weights are suitable for use in the present invention. Typically, chitosan materials for use herein have a molecular weight ranging from 1,000 to 10,000,000 grams per gram moles and more preferably from 2,000 to 1,000,000. Molecular weight means average molecular weight. Methods for determining the average molecular weight of chitosan materials are known to those skilled in the art. Typical methods include for example light scattering, intrinsic viscosity and gel permeation chromatography. It is generally most convenient to express the molecular weight of a chitosan material in terms of its viscosity in a 1.0 weight percent aqueous solution at 25° C. with a Brookfield viscometer. It is common to indirectly measure the viscosity of the chitosan material by measuring the viscosity of a corresponding chitosan salt, such as by using a 1.0 weight percent acetic acid aqueous solution. Chitosan materials suitable for use in the present invention will suitably have a viscosity in a 1.0 weight-% aqueous solution at 25° C. of from about 10 mPa·s (10 centipoise) to about 100,000 mPa·s (100,000 centipoise), more suitably from about 30 mPa·s (30 centipoise) to about 10,000 mPa·s (10,000 centipoise), even more suitably 7000 mPa·s (7000 centipoise).

The pH of the chitosan materials depends on their preparation. Preferred chitosan materials for use herein have an acidic pH, typically in the range of 3 to 7, preferably about 5. By pH of the chitosan material, it is meant herein the pH of a 1% chitosan material solution (1 gram of chitosan material dissolved in 100 grams of distilled water) measured by a pH-meter. By using a more acidic pH, the cationic character of the chitosan materials will be increased and thus their gelifying abilities. However, too high acidity is detrimental to skin safety. Thus it is highly preferred herein to use chitosan materials with a pH of about 5, thereby delivering the best compromise between fluid handling properties on one side and skin compatibility on the other side.

Particularly suitable chitosan materials for use herein are chitosan salts, especially water-soluble chitosan salts. A variety of acids can be used for forming chitosan salts. Suitable acids for use are soluble in water or partially soluble in water, are sufficiently acidic to form the ammonium salt of chitosan and yet not sufficiently acidic to cause hydrolysis of chitosan and are present in amount sufficient to protonate the reactive sites of chitosan.

Preferred acids can be represented by the formula:

wherein n has a value of 1 to 3 and R represents a mono- or divalent organic radical composed of carbon, hydrogen and optionally at least one of oxygen, nitrogen and sulphur or simply R is an hydrogen atom. Preferred acids are the mono- and dicarboxylic acids composed of carbon, hydrogen, oxygen and nitrogen (also called hereinafter amino acids). Such acids are highly desired herein as they are biologically acceptable for use against or in proximity to the human body. Illustrative acids, in addition to those previously mentioned include, among others, are citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, 2-pyrrolidone-5-carboylic acid, salycilic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid and thioglycolic acid. Any chitosan salts formed from the reaction of chitosan with any of these acids are suitable for use herein.

Examples of chitosan salts formed with an inorganic acid include, but are not limited to, chitosan hydrochloride, chitosan hydrobromide, chitosan phosphate, chitosan sulphonate, chitosan chlorosulphonate, chitosan chloroacetate and mixtures thereof. Examples of chitosan salts formed with an organic acid include, but are not limited to, chitosan formate, chitosan acetate, chitosan lactate, chitosan glycolate, chitosan malonate, chitosan epoxysuccinate, chitosan benzoate, chitosan adipate, chitosan citrate, chitosan salicylate, chitosan propionate, chitosan nitrilotriacetate, chitosan itaconate, chitosan hydroxyacetate, chitosan butyrate, chitosan isobutyrate, chitosan acrylate and mixtures thereof. It is also suitable to form a chitosan salt using a mixture of acids including, for example, both inorganic and organic acids.

Highly preferred chitosan salts for use herein are those formed by the reaction of chitosan with an amino acid. Amino acids are molecules containing both an acidic and amino functional group. The use of amino acids is highly preferred as those chitosan amino salts have higher skin compatibility. Indeed most of the amino acids are naturally present on the skin. Chitosan salts of pyrrolidone carboxylic acid are effective moisturizing agents and are non-irritating to skin. Amino acids for use herein include both linear and/or cyclo amino acids. Examples of amino acids for use herein include, but are not limited to, alanine, valine, leucine, isoleucine, prolinephenylalanine, triptofane, metionine, glycine, serine, cysteine, tyrosine, asparagine, glutamine, aspartic acid, glutamic acid, lysine, arginine, istydine, hydroxyproline and the like. A particularly suitable example of a cyclic amino acid is pyrrolidone carboxylic acid, which is a carboxylic acid of pyrrolidin-2-one as per following formula:

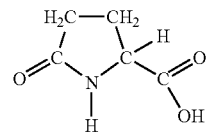

Other chitosan materials suitable for use herein include cross-linked chitosans with a low degree of cross-linkage and modified chitosans. Suitable crosslinking agents for use herein are organic compounds having at least two functional groups or functionalities capable of reacting with active groups located on the chitosan materials. Examples of such active groups include, but are not limited to, carboxylic acid (—COOH), amino (—NH$_2$), or hydroxyl (—OH) groups. Examples of such suitable crosslinking agents include, but are not limited to, diamines, polyamines, diols, polyols, dicarboxylic acids, polycarboxylic acids, aminocarboxylic acids, aminopolycarboxylic acids, polyoxides and the like. One way to introduce a crosslinking agent with the chitosan material solution is to mix the crosslinking agent with chitosan during preparation of the solution. Another suitable crosslinking agent comprises a metal ion with more than two positive charges, such as $Ca^{2+}$, $Al^{3+}$, $Fe^{3+}$, $Ce^{3+}$, $Ce^{4+}$, $Ti^{4+}$, $Zr^{4+}$ and $Cr^{3+}$. Since the cations on chitosan possess antimicrobial properties, it is preferred herein to not use a crosslinking agent reacting to the cations, unless no alternative crosslinking agent is available.

Suitable chitosan material is commercially available from numerous vendors. Exemplary of a commercially available chitosan materials are those available from for example the Vanson Company. The preferred chitosan salt for use herein is chitosan pyrrolidone carboxylate (also called chitosonium pyrrolidone carboxylate), which has a degree of deacetylation of more than 85%, a water solubility of 1% (1 gram is soluble in 100 grams of distilled water at 25° C. and one atmosphere) and a pH of about 5. Chitosonium pyrrolidone carboxylate is commercially available under the name Kytamer® PC from Amerchol Corporation. Another preferred chitosan salt for use herein is chitosan lactate, the chitosan salt of lactic acid, which is commercially available from Vanson Company, Redmond, Wash., USA.

Absorbent Structure and Absorbent Article Containing the Same

The term 'absorbent structure' is used herein to describe absorbent webs suitable for use in absorbent articles. The absorbent member comprises two surfaces aligned substantially opposite to each other. The first and the second surface are spaced apart from each other by the thickness dimension of the absorbent member. The absorbent member comprises the superabsorbent material of the present invention. The absorbent member according to the present invention can be used as absorbent core or so-called secondary topsheet or secondary backsheet in absorbent articles. The absorbent member typically has significant internal void space in the form of pores, holes, apertures, interstitial space between fibres and the like. Examples of absorbent members for use in the present invention are fibrous webs, such as nonwovens or fabrics, comprising natural or synthetic fibres or mixtures thereof, or apertured polymeric films or foam materials. Indeed, the absorbent member according to the present invention can be made of any of a variety of fibres, including a blend or admixture. The fibres may be cellulosic, modified cellulosic, or hydrophilic synthetic and include such fibres as wood pulp, rayon, cotton, cellulose acetate, polyester, nylon and the like. The absorbent member can be made according to any suitable method known for this purpose in the art. Fibrous absorbent members according to the present invention can be made by appropriate processes such as dry laying and in particular air laying, melt blowing or spunbonding. Film-like or foam-like absorbent members according to the present invention are made by processes suitable for such purposes. Highly preferred absorbent members for use herein are hydrophilic fibrous webs. As used herein, 'hydrophilic' refers to a material having a contact angle of water in air of less than 90 degrees, whereas the term 'hydrophobic' herein refers to a material having a contact angle of water in air of 90 degrees or greater. An absorbent member comprising hydrophilic fibres like for example cellulosic fibres such as wood pulp fibres is particularly useful in such products as sanitary napkins, disposable diapers or wipes because the hydrophilic fibres are liquid absorbent and therefore enhance the overall absorbency of the absorbent member. Preferably, absorbent members for use herein can be made of a blend of cellulosic and hydrophilic synthetic fibres, typically comprising about 65% to 95% by weight of cellulosic fibres and more preferably up to about 20% by weight of the hydrophilic synthetic fibres. The hydrophilic synthetic fibres, which can be provided in any length including staple length, can improve the strength of the absorbent member. Hydrophobic fibres or films, such as fibres or films made of polyethylene or polypropylene, may also be used in the absorbent member herein provided they are treated by e.g. surfactants to make them hydrophilic, in order not to decrease the absorbent capacity of the preferred absorbent member.

In other embodiments the absorbent structure is mainly made of foam material, into which the superabsorbent material is distributed.

In still further embodiments herein, the absorbent structure is mainly made of an adhesive, preferably a hot-melt adhesive, into which the superabsorbent material is distributed.

The absorbent structure of the present invention can be comprised of one layer only. Alternatively, the absorbent structure herein can also be comprised of multiple layers.

The superabsorbent material is in one embodiment relatively evenly distributed throughout the absorbent structure. In another embodiment herein, the superabsorbent material of the present invention is concentrated in a layer, which extends substantially parallel to the surfaces of the absorbent structure and is located between these surfaces.

In a preferred embodiment, the absorbent structure according to the present invention is used in the absorbent core of an absorbent article.

The term 'absorbent article' is used herein in a very broad sense including any article able to receive and/or absorb and/or contain and/or retain fluids and/or exudates, especially bodily fluids/bodily exudates. The absorbent article, which is referred to in the present invention typically comprises a fluid pervious topsheet, a fluid impervious backsheet that is preferably water vapour and/or gas pervious and an absorbent core comprised there between. Particularly preferred absorbent articles in the context of the present invention are disposable absorbent articles. Typical disposable absorbent articles according to the present invention are diapers, surgical and wound dressings and perspiration pads, incontinence pads, and preferably absorbent articles for feminine hygiene like sanitary napkins, panty liners, tampons, interlabial devices or the like.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. Superabsorbent material comprising multicomponent particles, said multicomponent particles being constituted of water-swellable, acidic superabsorbent resin particles having at least one microdomain on their surface, wherein said at least one microdomain is constituted by at least one gel-forming polysaccharide and said at least one microdomain has an average diameter ranging from about 1 nm to about 200 μm.

2. The superabsorbent material of claim 1, wherein said gel-forming polysaccharide is cationic.

3. The superabsorbent material of claim 1, wherein said gel-forming polysaccharide is acidic, having a pH of from about 3 to about 6.

4. The superabsorbent material of claim 1, wherein said gel-forming polysaccharide is an acidic chitosan salt, such as chitosonium pyrrolidone carboxylate, chitosonium lactate.

5. The superabsorbent material of claim 1, wherein said gel-forming polysaccharide is cross-linked.

6. The superabsorbent material of claim 1, wherein said particles of superabsorbent resin are made of a superabsorbent resin, such as partially neutralized polyacrylic acid, polylactic acid, poly(vinylphosphonic acid), poly(vinylphosphoric acid), poly(vinyl-sulfuric acid), carboxymethyl cellulose and starch-based absorbent materials.

7. The superabsorbent material of claim 6, wherein said acidic superabsorbent resin particles are made of a superabsorbent resin having a pH of from about 3.5 to about 6.

8. The superabsorbent material of claim 6, wherein said acidic superabsorbent resin particles are made from cross-linked superabsorbent resin.

9. The superabsorbent material of claim 6, wherein the weight ratio of said superabsorbent resin to said gel-forming polysaccharide ranges from about 90:10 to about 10:90.

10. The superabsorbent material of claim 1, wherein said acidic superabsorbent resin particles are present as granules having an average diameter ranging from about 10 μm to about 2 mm.

11. The superabsorbent material of claim 1, wherein said acidic superabsorbent resin particles are present as granules having an average diameter ranging from about 100 μm to about 1 mm.

12. The superabsorbent material of claim 1, wherein said at least one microdomain has an average diameter ranging from about 20 nm to about 100 μm.

13. The superabsorbent material of claim 1, wherein said at least one microdomain has an average diameter ranging from about 30 nm to about 1 μm.

14. The superabsorbent material of claim 1, wherein said at least one microdomain has an average diameter ranging from about 40 nm to about 800 nm.

15. The superabsorbent material of claim 1, wherein further microdomains are present in the interior of said multicomponent particles.

16. The superabsorbent material of claim 1, wherein the interior of said multicomponent particles is free of said microdomains.

17. Absorbent structure for use in absorbent articles for personal hygiene, comprising a carrier material and superabsorbent material,
wherein said superabsorbent material is the superabsorbent material of claim 1.

18. The absorbent structure of claim 17, wherein said carrier material is a fibrous material selected from hydrophilic fibres, hydrophobic fibres or combinations thereof.

19. The absorbent structure of claim 17, wherein said carrier material is an adhesive.

20. The absorbent structure of claim 17, wherein said carrier material is a hot-melt adhesive.

* * * * *